*(12)* United States Patent
Xiao et al.

(10) Patent No.: US 9,073,820 B2
(45) Date of Patent: Jul. 7, 2015

(54) PHARMACEUTICAL COMPOSITIONS COMPRISING NAPTHAMIDES

(71) Applicants: Xiangshu Xiao, Portland, OR (US); Bingbing Li, Portland, OR (US); Fuchun Xie, Portland, OR (US)

(72) Inventors: Xiangshu Xiao, Portland, OR (US); Bingbing Li, Portland, OR (US); Fuchun Xie, Portland, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 0 days.

(21) Appl. No.: 14/355,926

(22) PCT Filed: Nov. 2, 2012

(86) PCT No.: PCT/US2012/063361
§ 371 (c)(1),
(2) Date: May 2, 2014

(87) PCT Pub. No.: WO2013/067379
PCT Pub. Date: May 10, 2013

(65) Prior Publication Data
US 2014/0336262 A1    Nov. 13, 2014

Related U.S. Application Data

(60) Provisional application No. 61/555,783, filed on Nov. 4, 2011.

(51) Int. Cl.
C07C 235/66 (2006.01)
A61K 31/165 (2006.01)

(52) U.S. Cl.
CPC ............ *C07C 235/66* (2013.01); *A61K 31/165* (2013.01)

(58) Field of Classification Search
CPC .... C07C 15/24; C07C 235/66; A01B 12/006; A61K 31/165; A61K 31/166
See application file for complete search history.

(56) References Cited

U.S. PATENT DOCUMENTS

2010/0041638 A1    2/2010   Andrews

FOREIGN PATENT DOCUMENTS

WO       2010/048302       *   4/2010
WO       WO2010/048302 A1     4/2010

OTHER PUBLICATIONS

Nakayama, J of Biological Chemistry, vol. 288, No. 31, pp. 22584-22595, 2013.*
Daniel, Oncogenesis, vol. 3, pp. 1-10, 2014.*
Radhakrishnan et al. 'Conformational preferences in the Ser133-phosphorylated and non-phosphorylated forms of the kinase inducible transactivation domain of CREB', FEBS Letters, 1-20.1998, vol. 430, pp. 317-322.

* cited by examiner

*Primary Examiner* — D M Seaman
(74) *Attorney, Agent, or Firm* — Jeffrey M. Jackson

(57) ABSTRACT

Disclosed herein are naphthamide and quinoline carboxamide compounds containing two bicyclic moieties, pharmaceutical compositions comprising those compounds and methods of using the compositions in the treatment of cancers mediated by cyclic-AMP (cAMP) response element binding protein (CREB). The disclosed compositions have utility in the treatment of lung, prostate and breast cancers in a human subject.

20 Claims, 3 Drawing Sheets

PHARMACEUTICAL COMPOSITIONS COMPRISING NAPTHAMIDES

ACKNOWLEDGEMENT OF GOVERNMENT SUPPORT

This invention was made with US Federal Government support under grant number R01GM087305 awarded by the National Institutes of Health. The US Federal Government may have certain rights to the invention.

FIELD

Generally, the disclosure relates to pharmaceutical compositions. More specifically, the disclosure relates to pharmaceutical compositions comprising naphthamide compounds.

BACKGROUND

Cyclic-AMP (cAMP) response element binding protein (CREB) belongs to a large family of basic leucine zipper (bZIP)-containing transcription factors including c-Jun, c-Fos and c-Myc. The protein serves a variety of biological functions including cellular proliferation, differentiation and adaptive responses. These processes are mediated by selectively transcribing a subset of CREB target genes activated by phosphorylation of CREB at Ser133 by mitogen- or stress-activated protein kinases. The phosphorylated CREB (p-CREB) is then able to bind the mammalian transcription co-activator, CREB-binding protein (CBP), via the KID (kinase-inducible domain) domain in CREB and KIX (KID-interacting) domain in CBP. This binding event will further recruit other transcriptional machinery to initiate gene transcription. Recently, it was discovered that another family of transcription co-activators, transducers of regulated CREB (TORCs), cooperates with CBP to confer the selective activation of target genes in response to distinct cellular signals.

Recent studies have revealed that CREB is overexpressed in many different cancer cells and participates in the regulation of immortalization and transformation of normal cells. In human prostate cancer (PCa), immunohistochemical analysis of primary and bone metastatic prostate cancer tissue from patients demonstrated that normal or benign prostate glands showed no detectable p-CREB. On the other hand, positive p-CREB staining was detected in poorly-differentiated cancers and bone metastatic tissue specimens. The increased level of activated p-CREB was associated with increased transcription of a CREB target gene VEGF (vascular endothelial growth factor). This positive correlation between the level of p-CREB and the extent of tumor differentiation and metastasis suggests that CREB is involved in tumor progression and metastasis. Overexpression of CREB was also seen in cancer tissues from breast cancer patients, non-small-cell lung cancer (NSCLC) patients, and the blast cells from patients with acute myeloid leukemia (AML).

SUMMARY

Small molecule inhibitors of CREB-mediated gene transcription have not been explored as potential anticancer agents. Unlike kinases and other enzymes containing a deep, narrow active site that makes them readily targeted by small molecules, transcription factors like CREB have active sites that often span a long, shallow surface, creating practical challenges to rationally design small molecules to inhibit such binding interactions. Therefore, CREB, like many transcription factors has been considered an undruggable target. Small molecule inhibitors of CREB-mediated gene transcription, if developed, would represent a novel class of broad-spectrum anticancer agents.

Pharmaceutical compositions comprising a compound of the structure:

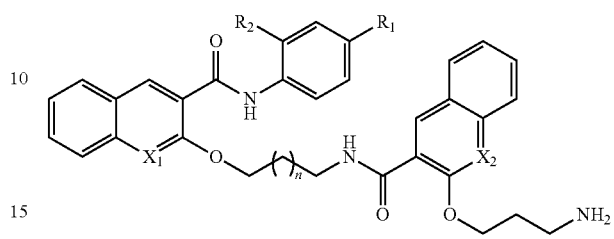

wherein n is an integer selected from 0 and 1, wherein $R_1$ is halo, wherein $R_2$ is OH or halo, and wherein $X_1$ and $X_2$ are independently CH or N.

Specific examples of the compositions include Compounds 4, 5, 6, 7, 8, and 9 described herein. These compounds have the following structures:

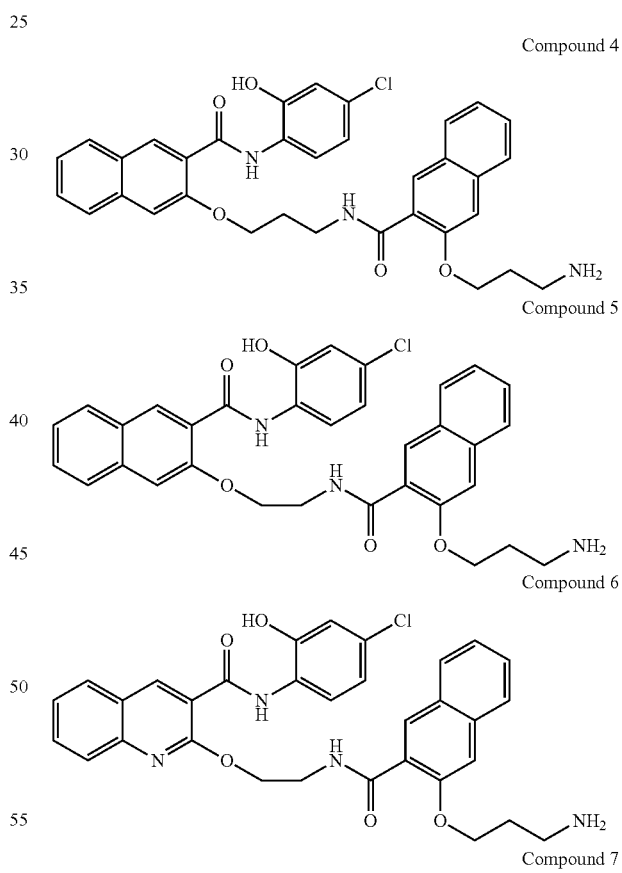

-continued

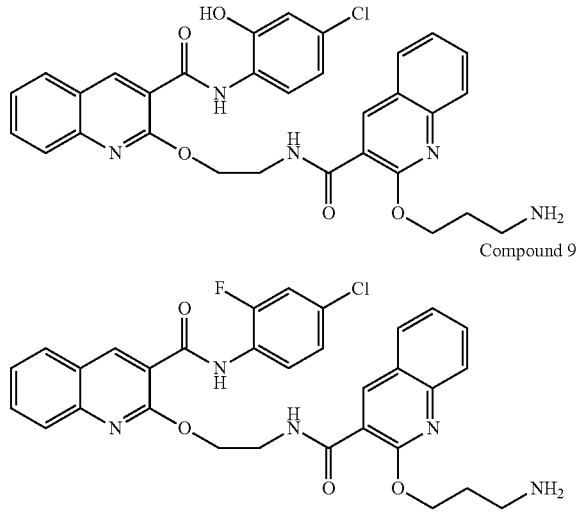

Compound 8

Compound 9

DETAILED DESCRIPTION

Figure 1:
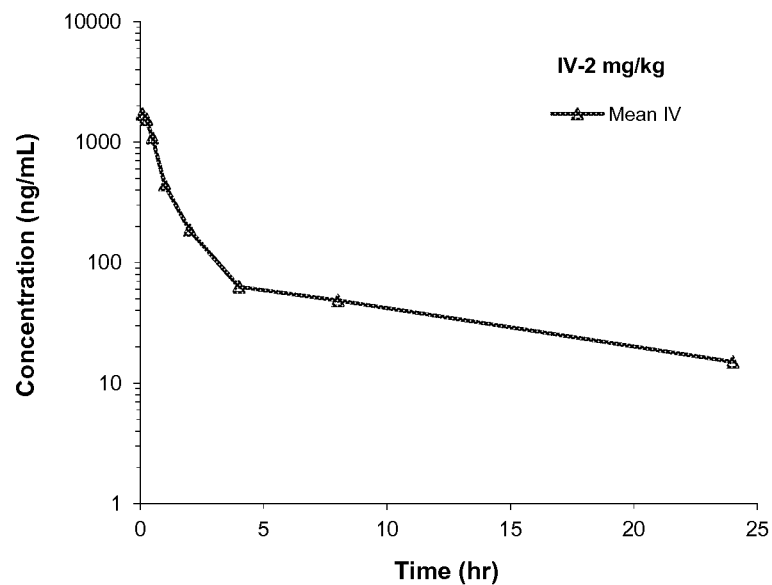
FIG. 1 is a graph depicting the clearance of a 2 mg/kg intravenous dose of Compound 4.

Disclosed herein are certain compounds, particularly naphthamides that can inhibit neoplasms and/or CREB-mediated gene transcription (particularly p-CREB/CBP interaction).

Pharmaceutical compositions comprising a compound of the formula are disclosed.

Methods of treating cancer comprising administering a pharmaceutical composition comprising the compound to a subject with cancer are disclosed.

Methods of manufacturing a medicament for use in the treatment of cancer comprising the compounds are disclosed.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Cancer" or "malignant neoplasm" includes a neoplasm that has undergone characteristic anaplasia with loss of differentiation, increased rate of growth, invasion of surrounding tissue, and which is capable of metastasis.

The term "halo" means a halogen (F, Cl, Br, I).

"Inhibiting" (which is inclusive of "treating") refers to inhibiting the full development of a disease or condition, for example, in a subject who is at risk for a disease such as hormone-resistant cancer. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology. By the term "coadminister" is meant that each of at least two compounds be administered during a time frame wherein the respective periods of biological activity overlap. Thus, the term includes sequential as well as coextensive administration of two or more drug compounds.

The terms "pharmaceutically acceptable salt" or "pharmacologically acceptable salt" refers to salts prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like.

Pharmaceutically acceptable salts of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977).

"Neoplasm" refers to an abnormal growth of cells or tissue, particularly a new growth of cells or tissue in which the growth is uncontrolled and progressive. A tumor is an example of a neoplasm.

The term "subject" includes both human and veterinary subjects.

A "therapeutically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount of an agent is an amount sufficient to inhibit or treat the disease without causing a substantial cytotoxic effect in the subject. The therapeutically effective amount will be dependent on the subject being treated, the severity of the affliction, and the manner of administration of the therapeutic composition.

"Tumor" refers to a mass of cells resulting from excessive cellular multiplication. A tumor is a neoplasm that may be either malignant or non-malignant (benign) and includes both solid and non-solid tumors (such as hematologic malignancies). As used herein, this term also encompasses other cell types found in the tumor microenvironment, such as vascular endothelial cells, pericytes, fibroblasts and/or other stromal elements.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Pharmaceutically acceptable prodrugs refer to compounds that are metabolized, for example, hydrolyzed or oxidized, in the subject to form an agonist compound re. Typical examples of prodrugs include compounds that have one or more biologically labile protecting groups on or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved either through routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In one example, a prodrug is a lower alkyl phosphonate ester such as an isopropyl phosphonate ester.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof. Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure. The compounds disclosed herein may be used to inhibit all types of cancer, tumor formation and metastasis in tumors. The compounds are particularly useful for inhibiting CREB-mediated cancers, neoplasms or diseases, which depend on CREB's transcription activity for survival, proliferation and/or metastasize. Illustrative cancers include lung cancer, prostate cancer, ovarian cancer, cervical cancer, breast cancer, melanoma, leukemia, liver cancer, thyroid cancer, uterine cancer, bladder cancer, bone cancer, colon cancer, central nervous system cancer, esophageal cancer, gall bladder cancer, gastrointestinal cancer, head and neck cancer, Hodgkin's Disease, non-Hodgkin's lymphomas, laryngeal cancer, neuroblastoma, pancreatic cancer, rectal cancer, renal cancer, retinoblastoma, stomach cancer, testicular cancer, myeloma, tonsil cancer, Wilms' tumor or a combination thereof.

The molecule may be administered to a subject for inhibiting a neoplasm in the subject.

The compounds disclosed herein may be included in pharmaceutical compositions (including therapeutic and prophylactic formulations), typically combined together with one or more pharmaceutically acceptable vehicles or carriers and, optionally, other therapeutic ingredients (for example, antibiotics or anti-inflammatories). The compositions disclosed herein may be advantageously combined and/or used in combination with other antiproliferative therapeutic agents, different from the subject compounds. In many instances, co-administration in conjunction with the subject compositions will enhance the efficacy of such agents. Exemplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof.

Such pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DLlactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly (epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent may be administered to a subject in need of such treatment for a time and under conditions sufficient to prevent, inhibit, and/or ameliorate a selected disease or condition or one or more symptom(s) thereof. Alternatively, an effective amount of the compound may be used to manufacture a pharmaceutical composition.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, CREB-mediated cancer) as discussed herein, or to determine the status of an existing disease or condition in a subject. These screening methods include, for example, diagnostic methods, such as various ELISA, western blot, immunohistochemical analysis, immunofluorescence staining, and real time RT-PCR analysis, which are available and well known in the art to detect and/or characterize disease-associated markers. These and other routine methods allow the clinician to select patients in need of therapy using the methods and pharmaceutical compositions of the disclosure.

The administration of the compound can be prophylactic or therapeutic. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

The following examples are illustrative of disclosed methods. In light of this disclosure, those of skill in the art will recognize that variations of these examples and other examples of the disclosed method would be possible without undue experimentation.

Example 1

Method of Synthesis of Compound 4

One example of a method of making a molecule to be included in a pharmaceutical composition from a precursor molecule is as follows:

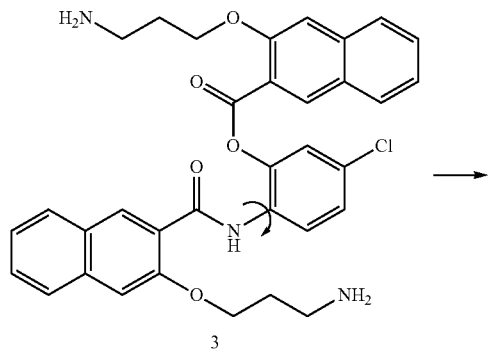

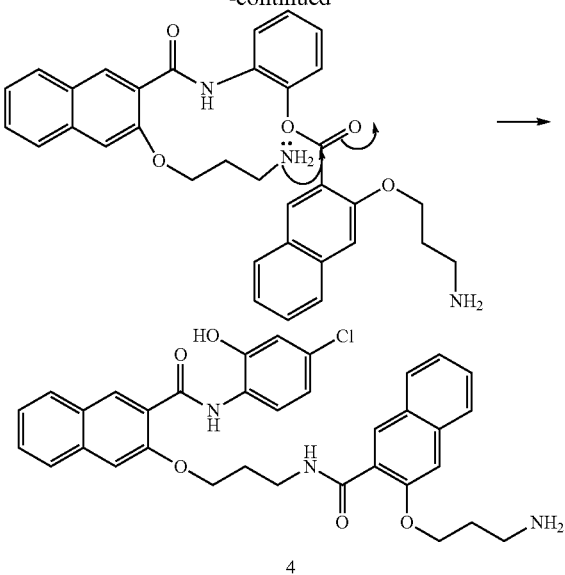

A solution of compound 3 (67 mg, 0.1 mmol) in PBS (pH=7.4, 2 mL) was stirred overnight at room temperature. Compound 3 is described in WO 2010/048302, which is incorporated by reference herein. A white precipitate formed during the stirring. The reaction mixture was neutralized with 5% NaHCO$_3$ (10 mL) and extracted with chloroform (50 mL). The organic layer was separated and dried over Na$_2$SO$_4$, filtered and concentrated to give a yellow solid. The solid was treated with chloroform and filtered to give the free base of compound 4 (30 mg, 50%) as a yellow solid: m.p. 206-207° C. $^1$H NMR (400 MHz, DMSO-d$_6$) δ 10.63 (brs, 2H, exchangeable with D$_2$O), 8.68(s, 1H), 8.57 (t, J=5.4 Hz, 1H, exchangeable with D$_2$O), 8.36 (d, J=8.5 Hz, 1H), 8.16 (s, 1H), 8.02 (d, J=7.9 Hz, 1H), 7.92 (d, J=7.9 Hz, 1H), 7.88 (d, J=8.4 Hz, 1H), 7.84 (d, J=7.9 Hz, 1H), 7.58 (s, 1H), 7.57 (t, J=7.3 Hz, 1H), 7.53 (t, J=7.1 Hz, 1H), 7.44 (s, 1H), 7.43 (t, J=7.1 Hz, 1H), 7.40 (t, J=7.8 Hz, 1H), 6.62 (d, J=2.4 Hz, 1H), 6.42 (dd, J=8.2, 2.3 Hz, 1H), 4.38 (t, J=7.2 Hz, 2H), 4.28 (t, J=5.3 Hz, 2H), 3.53 (q, J=6.7 Hz, 2H), 3.02 (t, J=6.9 Hz, 2H), 2.39 (quintet, J=7.3 Hz, 2H), 2.12 (quintet, J=5.9 Hz, 2H); $^{13}$C NMR (100 MHz, DMSO-d$_6$) δ 166.54, 161.86, 156.81, 154.02, 153.72, 135.91, 135.25, 133.27, 130.34, 129.25, 128.74, 128.58, 128.13, 128.08, 127.97, 127.92, 126.89, 126.81, 126.54, 125.04, 124.80, 123.83, 119.65, 114.70, 112.52, 108.19, 107.56, 67.96, 66.53, 37.54, 36.92, 29.03, 28.35.

An HCl solution in Et$_2$O (2 M, 3 mL) was added to a stirred solution of free base obtained above (20 mg, 0.033 mmol) in CHCl$_3$ (2 mL). The resulting mixture was stirred at room temperature for more than 8 hours. The solvent was removed under reduced pressure and the solid was treated with ethyl ether and filtered to give product 4 (15 mg, 71%) as a white solid: m.p. 189-190° C. $^1$H NMR (400 MHz, DMSO-d$_6$) δ11.01 (s, 1H, exchangeable with D$_2$O), 10.53 (s, 1H, partially exchangeable with D$_2$O), 8.73 (s, 1H), 8.62 (t, J=6.0 Hz, 1H, exchangeable with D$_2$O), 8.46 (d, J=8.7 Hz, 1H), 8.06 (s, 1H), 8.05 (d, J=8.5 Hz, 1H), 7.94 (brs, 3H, exchangeable with D$_2$O), 7.91 (d, J=8.1 Hz, 1H), 7.87 (d, J=8.2 Hz, 1H), 7.83 (d, J=8.4 Hz, 1H), 7.66 (s, 1H), 7.59 (t, J=7.8 Hz, 1H), 7.52 (t, J=7.4 Hz, 1H), 7.45 (t, J=7.7 Hz, 1H), 7.42 (s, 1H), 7.39 (t, J=7.1 Hz, 1H), 7.05 (d, J=2.2 Hz, 1H), 6.90 (dd, J=8.7, 2.1 Hz, 1H), 4.47 (t, J=5.9 Hz, 2H), 4.26 (t, J=5.6 Hz, 2H), 3.00 (q, J=5.9 Hz, 2H), 2.31 (quintet, J=6.0 Hz, 2H), 2.08 (quintet, J=5.8 Hz, 2H), a $CH_2$ was buried in water signal at 3.59 (note this $CH_2$ signal was shifted outside of water signal upon $D_2O$ addition); $^{13}C$ NMR (100 MHz, DMSO-$d_6$) δ 167.20, 162.67, 154.07, 153.50, 147.91, 136.12, 135.11, 133.54, 129.87, 129.39, 129.08, 128.59, 128.14, 128.04, 127.90, 127.59, 126.96, 126.91, 126.86, 126.47, 125.23, 124.89, 122.93, 121.53, 119.44, 114.77, 108.59, 1087.67, 67.63, 66.55, 37.30, 36.59, 28.94, 26.52.

Example 2

Efficacy of Compound 4

A549 (human lung cancer cells), MCF-7 (human breast cancer cells), MDA-MB-231 (human breast cancer cells) and MDA-MB-468 cells (human breast cancer cells) were maintained in Dulbecco's modified Eagle medium (DMEM, Invitrogen, Carlsbad, Calif.) supplemented with 10% (v/v) fetal calf serum (Sigma, St. Louis, Mo.), 10 µg/mL penicillin and 10 µg/mL streptomycin (Invitrogen, Carlsbad, Calif.) at 37° C. under 5% CO2. On the day of experiment, different concentrations of the drugs (final concentration $10^{-8}$-$10^{-4}$ M) in duplicates were added to the cells and the cells were further incubated for 72 h. Then, the number of live cells was quantified by 3-(4,5-dimethyl-2-thiazolyl)-2,5-diphenyl-2H-tetrazolium bromide (MTT reagent, Sigma, St. Louis, Mo.).

The amount of reduced MTT formazan generated by live cells was determined by its absorbance at 570 nm after subtracting the background absorbance at 690 nm. The percent of cell growth was expressed as $(A_{570(treated)}-A_{570(initial)})/(A_{570(vehicle\ treated)}-A_{570(initial)})*100$, where $A_{570(initial)}$ represents initial cell population when drugs are added. The $GI_{50}$ were derived from non-linear regression analysis of the dose-response curve using Prism 4.0 (GraphPad). Results are shown in Table 1. $GI_{50}$ represents concentrations at 50% growth inhibition. Data were presented as mean±SD of at least two measurements in duplicates unless noted.

Compound 4 inhibited CREB-mediated gene transcription in HEK 293T cells (Table 1). HEK293T cells in a 10-cm plate were transfected with pCRE-RLuc (6.0 µg) using Lipofectamine™ 2000 (Invitrogen, Carlsbad, Calif.) according to manufacturer's protocol. After 3 h, the transfected cells were collected and replated into 96-well plates (1-2×$10^4$ cells/well). The cells were allowed to attach to the bottom of the wells for overnight, when compounds of different concentrations were added to the cells. Forskolin (final concentration of 10 µM, LC Laboratories, Woburn, Mass.) was added 30 min after the addition of the compounds. The cells were then incubated at 37° C. for 5 h. The media in the wells were removed and the cells were then lysed in 30 µL of 1×Renilla luciferase lysis buffer (Promega, Madison, Wis.). To measure Renilla luciferase activity, five µL of the lysate was combined with 30 µL of benzyl-coelenterazine (Nanolight, Pinetop, Ariz.) solution in PBS (pH 7.4, 10 µg/mL). The sample protein concentration was determined by Dye Reagent Concentrate (Bio-Rad, Hercules, Calif.). The Renilla luciferase activity was normalized to protein content in each well and expressed as relative luciferase unit/µg protein (RLU/µg protein). The $IC_{50}$ was derived from non-linear regression analysis of the RLU/µg protein-concentration curve in Prism 5.0 (La Jolla, Calif.).

RLucC-KIX (15 ng) and KID-RLucN-containing cell lysates (0.5 mg) were mixed together in Renilla luciferase lysis buffer (Promega, Madison, Wis.) in the presence of different concentrations of compounds. The final volume of the incubation mixture is 30 µL. The mixture was incubated at 4° C. for 24 h. Then Renilla luciferase activity was measured by combining 5 µL of incubation mixture with 30 µL of coelenterazine solution in PBS (pH 7.4, 10 µg/mL). Results are shown in Table 1.

Compounds 1, 2, and 3 are described in WO/2010/048302, filed 21, Oct. 2009, which is hereby incorporated by reference herein.

Compound 1 has a structure of:

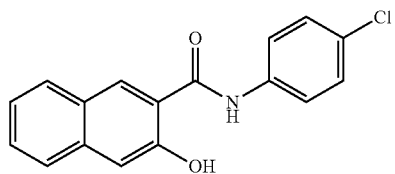 [SMILES: O=C(Nc1ccc(Cl)cc1)c1cc2ccccc2cc1O]

Compound 2 has a structure of:

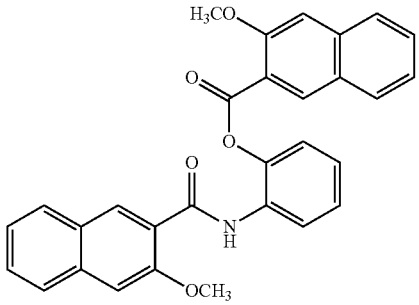 [SMILES: COc1cc2ccccc2cc1C(=O)Nc1ccccc1OC(=O)c1cc2ccccc2cc1OC]

Compound 3 has a structure of:

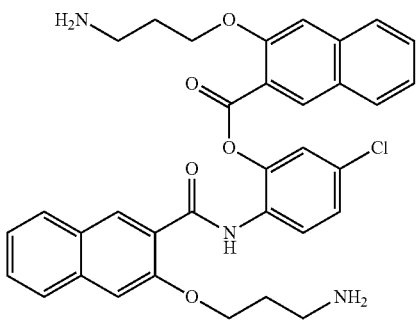 [SMILES: NCCCOc1cc2ccccc2cc1C(=O)Nc1ccc(Cl)cc1OC(=O)c1cc2ccccc2cc1OCCCN]

Table 1 shows the performance of compounds 1, 2, and 3 in comparison with Compounds 4, 5, 6, 7, 8, and 9 disclosed herein in the indicated assays. All values given in µM.

| Cmpd # | A549 ($GI_{50}$) | MCF-7 ($GI_{50}$) | MDA-MB-231 ($GI_{50}$) | MDA-MB-468 ($GI_{50}$) | CREB reporter inhibition ($IC_{50}$) | KIX-KID inhibition ($IC_{50}$) |
|---|---|---|---|---|---|---|
| 1 | 4.58 ± 1.52 | 2.56 ± 0.45 | 2.35 ± 0.60 | 1.46 ± 0.30 | 2.29 ± 0.31 | 2.90 ± 0.81 |
| 2 | 8.78 ± 2.55 | 3.38 ± 0.49 | 23.51 ± 2.27 | 8.13 ± 5.47 | 1.95 ± 1.14 | 0.17 ± 0.12 |
| 3 | 0.59 ± 0.02 | 0.42 ± 0.15 | $ND^a$ | $ND^a$ | 2.27 ± 0.28 | 8.02 ± 0.36 |
| 4 | 0.30 | 0.14 ± 0.029 | 0.23 ± 0.006 | 0.21 ± 0.071 | 2.22 ± 0.38 | 2.54 ± 0.28 |
| 5 | 0.47 ± 0.065 | 0.31 ± 0.10 | 0.073 ± 0.041 | 0.046 ± 0.039 | 0.081 ± 0.036 | $ND^a$ |
| 6 | $ND^a$ | $ND^a$ | 0.19 ± 0.12 | 0.013 ± 0.002 | 0.072 ± 0.009 | $ND^a$ |
| 7 | 0.64 | 0.19 | 0.84 ± 0.18 | 0.14 ± 0.024 | 0.17 ± 0.066 | $ND^a$ |
| 8 | $ND^a$ | $ND^a$ | 0.54 ± 0.13 | 0.29 ± 0.055 | 4.03 ± 0.20 | $ND^a$ |
| 9 | $ND^a$ | $ND^a$ | 0.37 ± 0.25 | $ND^a$ | 0.44 ± 0.34 | $ND^a$ |

$^a$ND: not determined.

Example 3

Pharmacokinetics of Compound 4

The pharmacokinetics of Compound 4 was assessed in BALB/c nude female mice. Doses were 2 mg/kg administered intravenously (IV) and 20 mg/kg administered orally (PO). The intravenous formulation was administered in 1% N-Methyl-2-pyrrolidone (NMP) in water and was a clear solution. The per os solution was in 1.3% NMP+5% Tween-20® in a clear solution.

Following IV administration, the elimination half life of Compound 4 ($t_{1/2}$) was 9.6 hours for a clearance rate of 12.7 (ml/min)/kg. Maximum plasma concentration was 335.4 ng/ml and was achieved at 1.0 hour after oral administration. Oral bioavailability was 7.1%.

TABLE 2

Plasma concentrations of IV administered compound 4.
Concentrations (G1, G2, G3) are given in ng/ml.

| IV Time (hr) | G1 | G2 | G3 | Mean IV | | S.D. | CV (%) |
|---|---|---|---|---|---|---|---|
| 0.083 | 1605.9 | 1978.0 | 1537.0 | 1707.0 | ± | 237.2 | 13.9 |
| 0.25 | 1140.3 | 1902.9 | 1609.1 | 1550.8 | ± | 384.6 | 24.8 |
| 0.5 | 1126.4 | 965.6 | 1170.5 | 1087.5 | ± | 107.8 | 9.9 |
| 1 | 528.0 | 378.0 | 418.6 | 441.5 | ± | 77.6 | 17.6 |
| 2 | 274.8 | 178.3 | 105.3 | 186.1 | ± | 85.0 | 45.7 |
| 4 | 59.9 | 71.0 | 58.1 | 63.0 | ± | 7.0 | 11.1 |
| 8 | 30.2 | 58.7 | 56.6 | 48.5 | ± | 15.9 | 32.7 |
| 24 | 15.3 | 16.4 | 13.3 | 15.0 | ± | 1.6 | 10.5 |

Totals

| | |
|---|---|
| $t_{1/2}$ (hr) | 9.6 |
| $AUC_{0-t}$ (ng · hr/mL) | 2423.1 |
| $AUC_{0-\infty}$ (ng · hr/mL) | 2630.8 |
| Cl (mL/min/kg) | 12.7 |
| Vss (L/Kg) | 4.8 |

TABLE 3

Plasma concentrations of PO (orally) administered compound 4.
Concentrations G4, G5, and G6 are given in ng/ml.

| PO Time (hr) | G4 | G5 | G6 | Mean PO | | S.D. | CV (%) |
|---|---|---|---|---|---|---|---|
| 0.25 | 75.5 | 92.7 | 100.8 | 89.7 | ± | 12.9 | 14.4 |
| 0.5 | 92.0 | 82.4 | 166.3 | 113.6 | ± | 45.9 | 40.4 |
| 1 | 402.4 | 465.2 | 138.6 | 335.4 | ± | 173.3 | 51.7 |
| 2 | 352.8 | 75.0 | 268.8 | 232.2 | ± | 142.5 | 61.4 |
| 4 | 128.1 | 65.9 | 118.1 | 104.0 | ± | 33.4 | 32.1 |
| 8 | 45.8 | 30.1 | 41.7 | 39.2 | ± | 8.1 | 20.8 |
| 12 | 46.0 | 47.6 | 48.2 | 47.3 | ± | 1.1 | 2.4 |
| 24 | 7.2 | 12.9 | 34.1 | 18.1 | ± | 14.2 | 78.5 |

Totals:

| | |
|---|---|
| $C_{max}$ (ng/mL) | 335.4 |
| $T_{max}$ (hr) | 1.0 |
| $t_{1/2}$ (hr) | 9.1 |
| $AUC_{0-t}$ (ng · hr/mL) | 1620.7 |
| $AUC_{0-\infty}$ (ng · hr/mL) | 1858.1 |
| Bioavailability | 7.1% |

Figure 2:
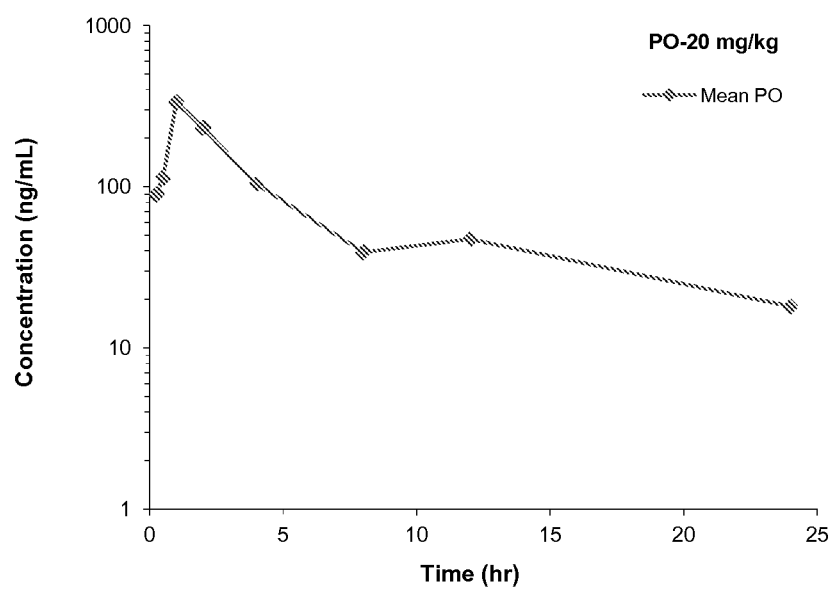
FIG. 2 is a graph depicting the clearance of a 20 mg/kg per os (oral) dose of Compound 4.
Figure 3:
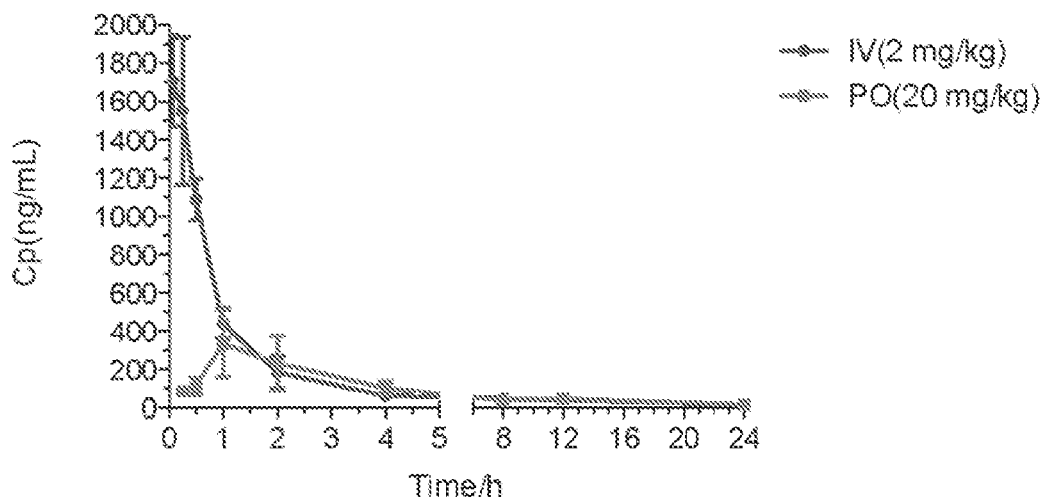
FIG. 3 is a graph depicting the clearance of a 2 mg/kg intravenous dose of Compound 4 superimposed on the clearance of a 20 mg/kg per os dose of Compound 4.

FIG. 1 shows time course of the plasma concentration (Cp) of intravenously administered compound 4. FIG. 2 time course of the plasma concentration ((Cp) of orally administered compound 4. FIG. 3 combines the Cp-time curves of both IV and orally administered compound 4.

Example 4

Maximum Tolerated Dose of Compound 4 (Body Weight)

The maximum tolerated dose (MTD) of compound 4 was evaluated in nude mice. In this study 4 groups were established, each with five mice per group. The compound was formulated in a suspension of 5% Tween-80/$H_2O$. Compound 4 was administered orally at dose levels of 120, 60, and 30 mg/kg as QD for five days. The body weight was measured daily for a total of 11 days.

Figure 4:
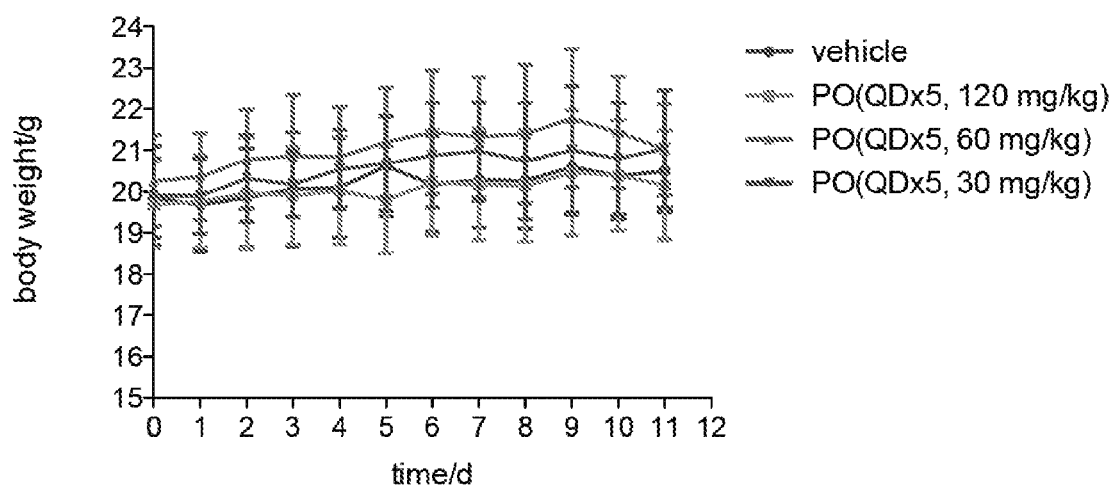
FIG. 4 is a graph depicting the effect of the indicated per os doses of Compound 4 on the weight of mice over time.

FIG. 4 shows that compound 4 is no different from vehicle with regard to its effect on mouse body weight. Doses as high as 120 mg/kg administered per os were well-tolerated.

Example 5

Antitumor Efficacy of Compound 4 in MDA-MB-231 Xenograft

Figure 5:
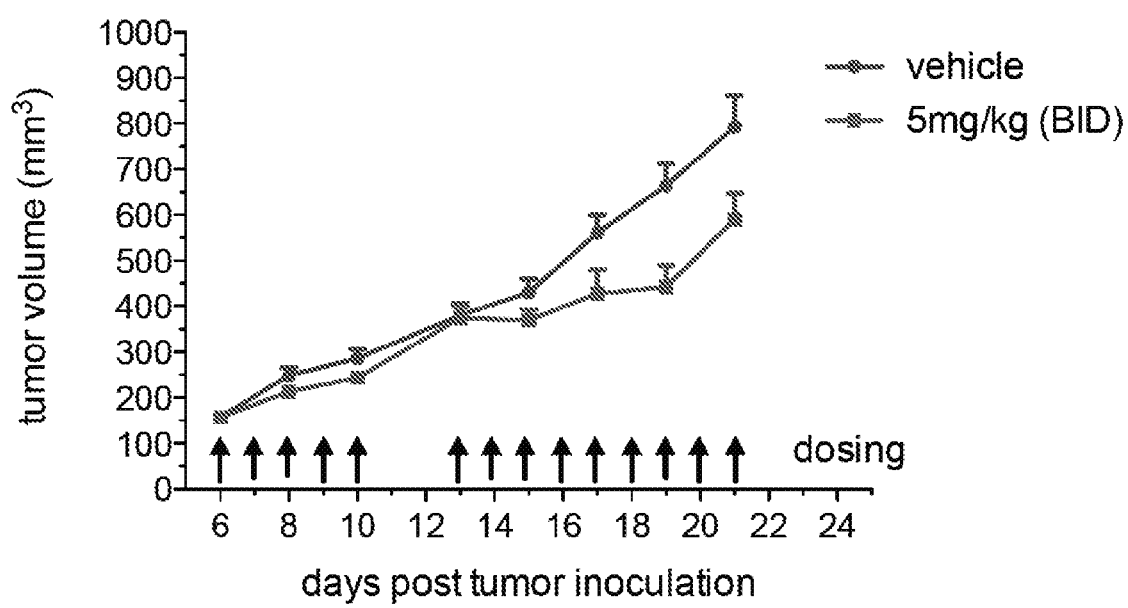
FIG. 5 is a graph depicting the antitumor efficacy of compound 4 in MDA-MB-231 xenograft.

Mice were inoculated orthotopically at the right mammary pad with MDA-MB-231 tumor cells ($1 \times 10^7$) in 0.1 ml of PBS with Matrigel (1:1) for tumor development. The treatments were started when the mean tumor size reached 157 $mm^3$. Compound 4 at 5 mg/kg was administered to the tumor-bearing mice by intraperitoneal injection. Tumor sizes were measured three times weekly in two dimensions using a digital caliper, and the volume was expressed in $mm^3$ using the formula: V=0.5 a×$b^2$ where a and b were the long and short diameters of the tumor, respectively. The date of tumor cell inoculation was denoted as day 0. Results are shown in FIG. 5.

Example 6

Synthesis of Compound 5 and Compound 7

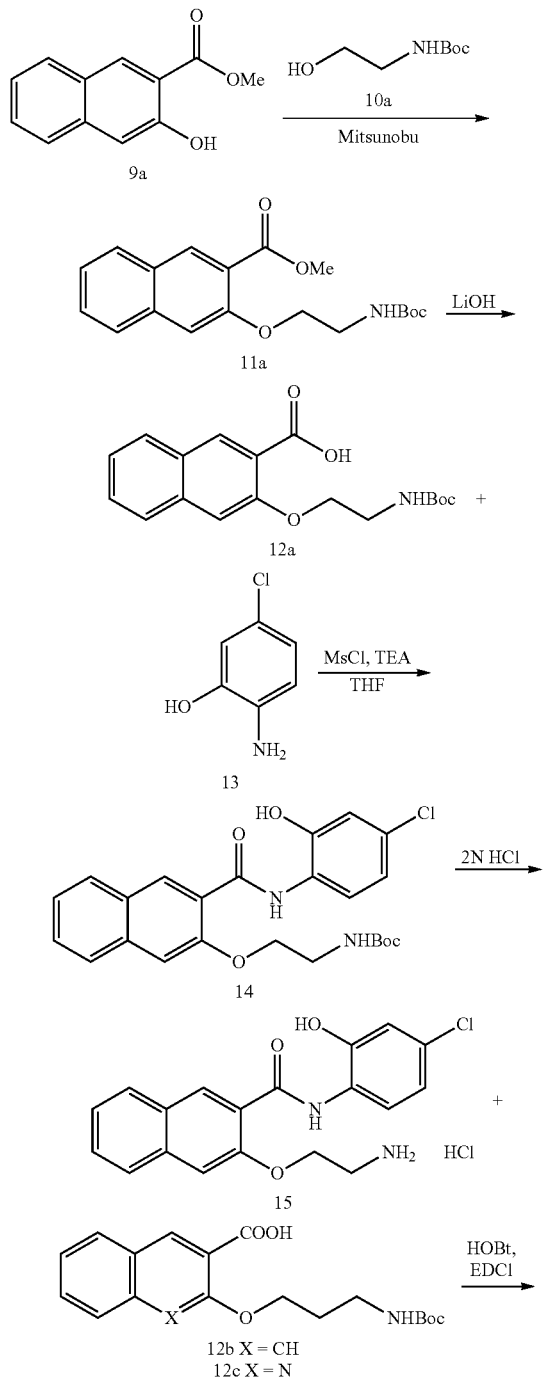

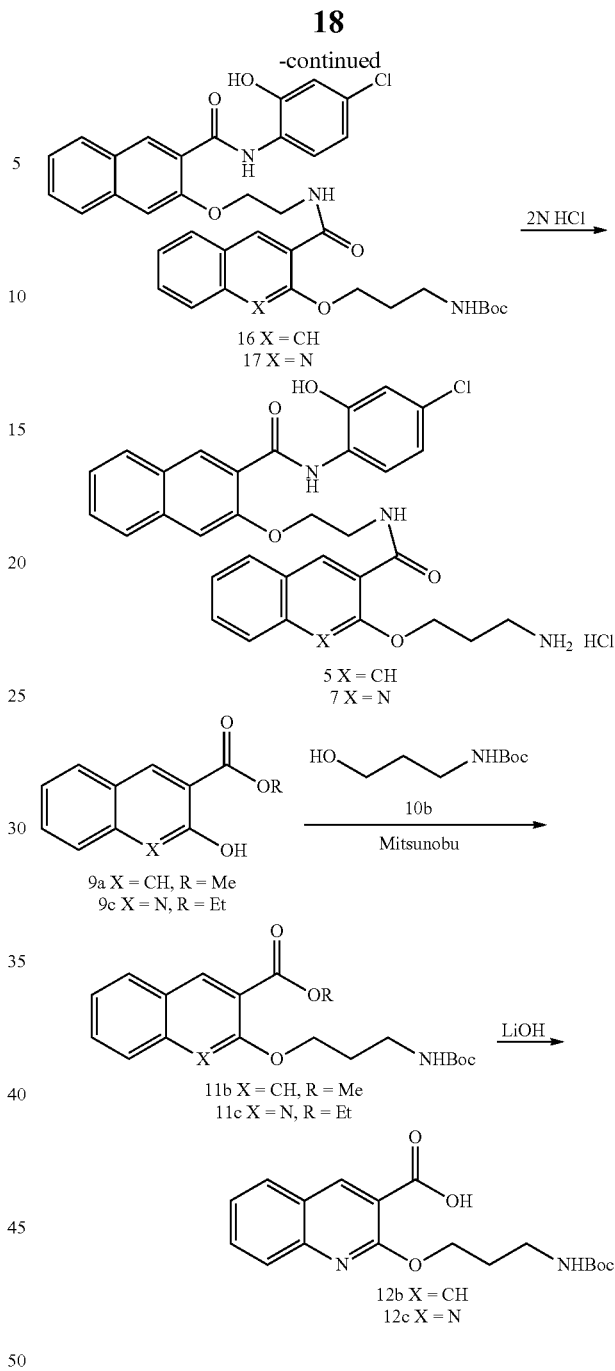

Compound 11a. To a solution of methyl 3-hydroxy-2-naphthoate 9a (3.65 g, 18 mmol), tert-butyl (2-hydroxyethyl) carbamate 10a (3.5 g, 21.7 mmol) and $PPh_3$ (5.69 g, 21.7 mmol) in THF (30 mL) was added DEAD (3.41 mL, 21.7 mmol in 8 mL THF) dropwise at 0° C. The mixture was stirred at room temperature for overnight. The solvent was removed under reduced pressure and the residue was purified by flash column chromatography, eluting with hexanes-dichloromethane-ethyl acetate (4:1:1) to give the product 11a (5.0 g, 81%) as an oil, which solidified upon standing. $^1$H NMR (400 MHz, $CDCl_3$) δ 8.36 (s, 1H), 7.83 (d, J=8.2 Hz, 1H), 7.73 (d, J=8.3 Hz, 1H), 7.53 (td, J=7.5, 1.2 Hz, 1H), 7.39 (td, J=7.4, 1.1 Hz, 1H), 7.20 (s, 1H), 5.58 (brs, 1H), 4.22 (t, J=5.0 Hz, 2H), 3.98 (s, 3H), 3.64 (q, J=5.1 Hz, 2H), 1.46 (s, 9H).

Compound 12a. To a solution of 11a (5.0 g, 14.5 mmol) in MeOH-THF-water (20 mL-30 mL-20 mL) was added $LiOH·H_2O$ (3.05 g, 72.5 mmol). The resulting mixture was stirred at room temperature for overnight. The solvent was removed under reduced pressure and the residue was acidified with con. HCl (7 mL) at 0° C., extracted with ethyl acetate (80 mL), washed with brine (30 mL), and dried over Na$_2$SO$_4$. The solvent was evaporated and the solid was treated with ethyl ether and collected by filtration to give the product 12a as a white solid (4.3 g, 90%). $^1$H NMR (400 MHz, DMSO-d$_6$) δ 12.83 (s, 1H), 8.23 (s, 1H), 7.94 (d, J=8.3 Hz, 1H), 7.84 (d, J=8.2 Hz, 1H), 7.55 (td, J=7.6, 1.3 Hz, 1H), 7.48 (s, 1H), 7.40 (td, J=7.4, 1.2 Hz, 1H), 4.13 (t, J=6.1 Hz, 2H), 3.37 (q, J=5.8 Hz, 2H), 1.38 (s, 9H).

Compound 14. To a suspension of 12a (4.6 g, 13.9 mmol) and TEA (1.94 mL, 13.9 mmol) in THF (60 mL) was added MsCl (1.1 mL, 13.9 mmol) dropwise at 0° C. The reaction mixture was stirred for 30 min at 0° C., then 2-amino-5-chlorophenol 13 (1.99 g, 13.9 mmol) was added and stirred for overnight. The reaction mixture was diluted with 5% NaHCO$_3$ (30 mL) and extracted with ethyl acetate (100 mL). The organic phase was washed with water (30 mL), 2N HCl (30 mL) and brine (30 mL) and dried over Na$_2$SO$_4$. The solvent was filtered and concentrated to give a light yellow solid. The solid was treated with ethyl acetate (25 mL) and filtered to give the pure compound 14 (4.2 g, 66%) as an orange solid. $^1$H NMR (400 MHz, DMSO-d$_6$) δ 10.87 (s, 1H), 10.46 (s, 1H), 8.72 (s, 1H), 8.44 (d, J=8.5 Hz, 1H), 8.04 (d, J=7.7 Hz, 2H), 7.90 (d, J=8.4 Hz, 1H), 7.66 (s, 1H), 7.60 (t, J=7.5 Hz, 1H), 7.45 (t, J=7.5 Hz, 1H), 7.07 (t, J=5.7 Hz, 1H), 6.96 (d, J=2.3 Hz, 1H), 6.91 (dd, J=8.4, 2.2 Hz, 1H), 4.31 (t, J=6.5 Hz, 2H), 3.59 (q, J=6.2 Hz, 2H), 1.35 (s, 9H). $^{13}$C NMR (100 MHz, DMSO-d$_6$) δ 162.01, 155.66, 153.18, 147.74, 135.64, 133.15, 128.89, 128.49, 127.64, 126.99, 126.43, 126.23, 124.73, 122.34, 121.08, 118.79, 114.31, 108.19, 90.16, 77.96, 67.94, 28.13.

Compound 15. An HCl solution in Et$_2$O (2 M, 30 mL) was added to a stirred solution of 14 (4.2 g, 9.2 mmol) in CHCl$_3$-MeOH (40 mL-40 mL). The resulting mixture was stirred at room temperature for overnight. The solvent was removed under reduced pressure and the solid was treated with acetone and filtered to give product 15 (3.0 g, 83%) as a white solid. $^1$H NMR (400 MHz, DMSO-d$_6$) δ 11.05 (s, 1H), 10.29 (s, 1H), 8.68 (s, 1H), 8.41 (d, J=8.6 Hz, 1H), 8.28 (brs, 3H), 8.06 (d, J=8.0 Hz, 1H), 7.94 (d, J=8.2 Hz, 1H), 7.66 (s, 1H), 7.61 (td, J=7.6, 1.3 Hz, 1H), 7.47 (td, J=7.6, 1.0 Hz, 1H), 7.03 (d, J=2.7 Hz, 1H), 6.93 (dd, J=8.5, 2.5 Hz, 1H), 4.56 (t, J=4.9 Hz, 1H), 3.51-3.46 (m, 2H). $^{13}$C NMR (100 MHz, DMSO-d$_6$) δ 162.16, 152.71, 147.80, 135.41, 132.98, 128.86, 128.55, 127.79, 127.01, 126.49, 126.37, 124.93, 123.07, 121.17, 118.88, 114.63, 108.18, 65.88, 38.23.

Compound 12b. To a solution of 11b (17.5 g, 48.7 mmol) in MeOH-THF-water (100 mL-200 mL-150 mL) was added LiOH.H$_2$O (10.25 g, 244 mmol). The resulting mixture was stirred at room temperature for overnight. The solvent was removed under reduced pressure and the residue was acidified with con. HCl (30 mL) at 0° C., extracted with chloroform (1000 mL), washed with brine (200 mL), and dried over Na$_2$SO$_4$. The solvent was evaporated and the solid was treated with ethyl ether and collected by filtration to give the product 12b as a white solid (15 g, 89%). $^1$H NMR (400 MHz, DMSO-d$_6$) 512.78 (brs, 1H), 8.21 (s, 1H), 7.93 (d, J=8.3 Hz, 1H), 7.83 (d, J=8.1 Hz, 1H), 7.54 (t, J=7.2 Hz, 1H), 7.42 (s, 1H), 7.39 (t, J=8.1 Hz, 1H), 6.91 (t, J=5.3 Hz, 1H), 4.14 (t, J=6.2 Hz, 2H), 3.15 (q, J=6.4 Hz, 2H), 1.90 (quintet, J=6.5 Hz, 2H), 1.37 (s, 9H).

Compound 12c. To a solution of 11c (120 mg, 0.32 mmol) in MeOH-THF-water (1:1:1, 9 mL) was added LiOH·H$_2$O (68 mg, 1.6 mmol). The resulting mixture was stirred at room temperature for overnight. The organic solvents were removed under reduced pressure and the residue was acidified with 2 N HCl to pH ~2 at 0° C. The reaction mixture was extracted with ethyl acetate (40 mL). The organic layer was then washed with brine (15 mL), and dried over Na$_2$SO$_4$. The solution was filtered and the solvent was removed to give product 12c (114 mg, 100%) as a white solid. $^1$H NMR (400 MHz, DMSO-d$_6$) δ 13.16 (s, 1H), 8.70 (s, 1H), 8.01 (d, J=8.0 Hz, 1H), 7.80-7.73 (m, 2H), 7.50-7.46 (m, 1H), 6.92 (t, J=5.4 Hz, 1H), 4.46 (t, J=6.5 Hz, 2H), 3.13 (q, J=6.4 Hz, 2H), 1.89 (quintet, J=6.5 Hz, 2H), 1.35 (s, 9H).

Compound 16. EDCl (269 mg, 1.23 mmol) and HOBt (183 mg, 1.23 mmol) were added to a stirred suspension of 15 (483 mg, 1.23 mmol) and 12b (422 mg, 1.23 mmol) in dichloromethane (20 mL) at room temperature. The reaction mixture was stirred for overnight at room temperature. The reaction mixture was then diluted with 5% NaHCO$_3$ (20 mL), which was extracted with dichloromethane (60 mL). The organic layer was washed with brine (20 mL) and dried over Na$_2$SO$_4$. The solution was filtered and the solvent was removed to give a residue that was treated with ethyl acetate (20 mL). The precipitate was collected by filtration to give pure product 16 (440 mg, 52%) as a white solid. $^1$H NMR (400 MHz, DMSO-d$_6$) δ 10.95 (s, 1H), 10.59 (s, 1H), 8.75 (s, 1H), 8.65 (t, J=4.9 Hz, 1H), 8.47 (d, J=8.5 Hz, 1H), 8.29 (s, 1H), 8.05 (d, J=8.5 Hz, 1H), 7.89 (d, J=8.1 Hz, 1H), 7.87 (d, J=8.3 Hz, 1H), 7.81 (d, J=8.2 Hz, 1H), 7.70 (s, 1H), 7.59 (t, J=7.2 Hz, 1H), 7.52 (t, J=7.6 Hz, 1H), 7.45 (t, J=7.1 Hz, 1H), 7.41 (s, 1H), 7.38 (t, J=7.6 Hz, 1H), 6.93-6.83 (m, 3H), 4.52 (t, J=5.8 Hz, 2H), 4.10 (t, J=5.6 Hz, 2H), 4.05 (q, J=5.2 Hz, 2H), 3.01 (t, J=6.3 Hz, 2H), 1.81 (quintet, J=6.2 Hz, 2H), 1.23 (s, 9H); $^{13}$C NMR (100 MHz, DMSO-d$_6$) δ 165.44, 161.97, 155.69, 153.48, 153.19, 147.69, 135.67, 135.04, 133.26, 131.08, 128.93, 128.52, 128.40, 127.82, 127.69, 127.38, 127.00, 126.46, 126.32, 126.20, 124.77, 124.64, 124.28, 122.23, 120.92, 118.80, 114.22, 108.27, 107.30, 77.52, 67.78, 65.76, 38.41, 36.54, 28.67, 28.03.

Compound 17. DIPEA (58 μL, 0.33 mmol), EDCl (73 mg, 0.33 mmol) and HOBt (50 mg, 0.33 mmol) were added to a stirred suspension of 12c (114 mg, 0.3 mmol) and 15 (130 mg, 0.33 mmol) in dichloromethane (5 mL) at room temperature. The reaction mixture was stirred for overnight at room temperature. The reaction mixture was then diluted with water (20 mL) and was extracted with ethyl acetate (50 mL). The organic layer was washed with brine (20 mL) and dried over Na$_2$SO$_4$. The solution was filtered and the solvent was removed to give a residue that was purified by flash column chromatography, eluting with dichloromethane-ethyl acetate (5:1) to give the product 17 (140 mg, 68%) as a white solid. $^1$H NMR (400 MHz, DMSO-d$_6$) δ 10.93 (s, 1H), 10.58 (s, 1H), 8.78-8.73 (m, 2H), 8.70 (s, 1H), 8.45 (d, J=8.3 Hz, 1H), 8.05 (d, J=8.1 Hz, 1H), 7.96 (d, J=7.6 Hz, 1H), 7.90 (d, J=7.8 Hz, 1H), 7.77-7.73 (m, 2H), 7.70 (s, 1H), 7.59 (t, J=7.6 Hz, 1H), 7.50-7.42 (m, 2H), 6.90-6.80 (m, 3H), 4.54 (t, J=5.8 Hz, 2H), 4.41 (t, J=6.2 Hz, 2H), 4.05 (q, J=5.7 Hz, 2H), 2.99 (q, J=6.1 Hz, 2H), 1.77 (quintet, J=6.3 Hz, 2H), 1.23 (s, 9H); $^{13}$C NMR (100 MHz, DMSO-d$_6$) δ 163.89, 161.95, 157.74, 155.71, 153.13, 147.60, 146.25, 141.32, 135.66, 133.27, 131.40, 128.93, 128.74, 128.54, 127.70, 126.99, 126.45, 126.29, 126.15, 124.79, 124.16, 122.24, 120.91, 118.81, 118.71, 114.18, 108.31, 77.49, 67.72, 63.71, 38.49, 36.45, 28.61, 28.03.

Compound 5. An HCl solution in Et$_2$O (2 M, 15 mL) was added to a stirred solution of 16 (1.7 g, 2.485 mmol) in CHCl$_3$-MeOH (20 mL-20 mL). The resulting mixture was stirred at room temperature for overnight. The solvent was removed under reduced pressure and the solid was treated with acetone (10 mL), filtered to give product 5 (1.4 g, 89%)

as a white solid. $^1$H NMR (400 MHz, DMSO-$d_6$) δ11.05 (s, 1H), 10.59 (s, 1H), 8.78 (t, J=5.7 Hz, 1H), 8.75 (s, 1H), 8.47 (d, J=9.1 Hz, 1H), 8.07 (d, J=8.7 Hz, 1H), 8.05 (s, 1H), 7.93 (d, J=8.3 Hz, 1H), 7.90 (brs, 3H), 7.83 (d, J=8.3 Hz, 1H), 7.74 (s, 1H), 7.72 (d, J=7.7 Hz, 1H), 7.61 (td, J=7.6, 1.1 Hz, 1H), 7.53 (td, J=7.6, 1.2 Hz, 1H), 7.46 (td, J=7.5, 1.0 Hz, 1H), 7.43 (s, 1H), 7.38 (td, J=7.6, 1.2 Hz, 1H), 7.02 (d, J=2.2 Hz, 1H), 6.92 (dd, J=8.7, 2.4 Hz, 1H), 4.53 (t, J=6.2 Hz, 2H), 4.24 (t, J=5.7 Hz, 2H), 3.96 (q, J=5.9 Hz, 2H), 3.01-2.93 (m, 2H), 2.06 (quintet, J=6.3 Hz, 2H); $^{13}$C NMR (100 MHz, DMSO-$d_6$) δ 166.56, 162.10, 153.12, 153.05, 147.76, 135.65, 134.77, 133.19, 130.00, 128.93, 128.56, 128.15, 127.78, 127.70, 127.36, 127.04, 126.50, 126.41, 125.69, 124.81, 124.39, 122.44, 120.98, 118.83, 114.41, 108.36, 107.32, 67.46, 65.99, 38.41, 36.84, 26.14.

Compound 7. An HCl solution in Et2O (2 M, 2 mL) was added to a stirred solution of 17 (110 mg, 0.16 mmol) in CHCl3-MeOH (3 mL-3 mL). The resulting mixture was stirred at room temperature for overnight. The solvent was removed under reduced pressure and the solid was treated with acetone (5 mL). The resulting solid was collected by filtration to give product 7 (67 mg, 68%) as a white solid. 1H NMR (400 MHz, DMSO-d6) δ 11.13 (s, 1H), 10.58 (s, 1H), 8.83 (t, J=5.6 Hz, 1H), 8.74 (s, 1H), 8.54 (s, 1H), 8.44 (d, J=8.5 Hz, 1H), 8.10-8.01 (m, 4H), 7.94 (d, J=8.2 Hz, 1H), 7.86 (d, J=8.0 Hz, 1H), 7.79-7.90 (m, 3H), 7.60 (t, J=7.6 Hz, 1H), 7.47 (t, J=7.9 Hz, 1H), 7.45 (t, J=7.3 Hz, 1H), 7.05 (d, J=2.2 Hz, 1H), 6.88 (dd, J=8.6, 2.2 Hz, 1H), 4.56-4.50 (m, 4H), 2.94 (q, J=5.7 Hz, 2H), 2.07 (quintet, J=6.1 Hz, 2H) (the signal of one CH2 group is masked by water peak); 13C NMR (100 MHz, DMSO-d6) δ 164.68, 162.05, 157.58, 153.09, 147.76, 146.03, 140.42, 135.65, 133.17, 131.29, 128.89, 128.56, 128.52, 127.69, 127.00, 126.51, 126.36, 126.18, 124.86, 124.79, 124.07, 122.41, 120.91, 119.54, 118.76, 114.42, 108.39, 67.46, 63.66, 38.45, 36.48, 26.18.

Example 7

Synthesis of Compound 6 and Compound 8

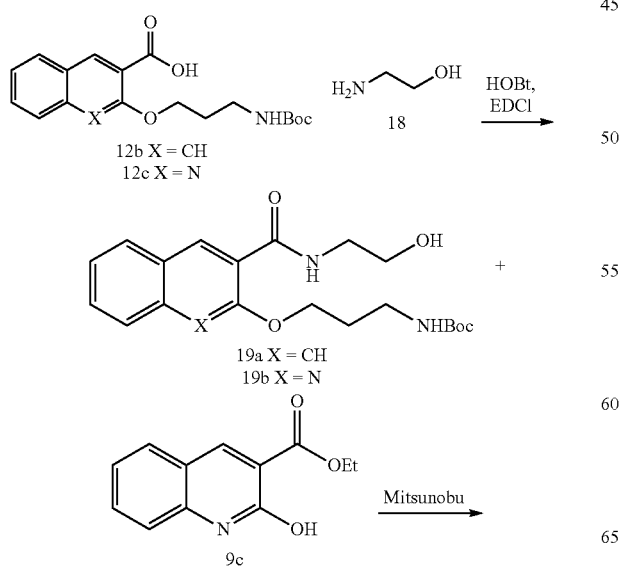

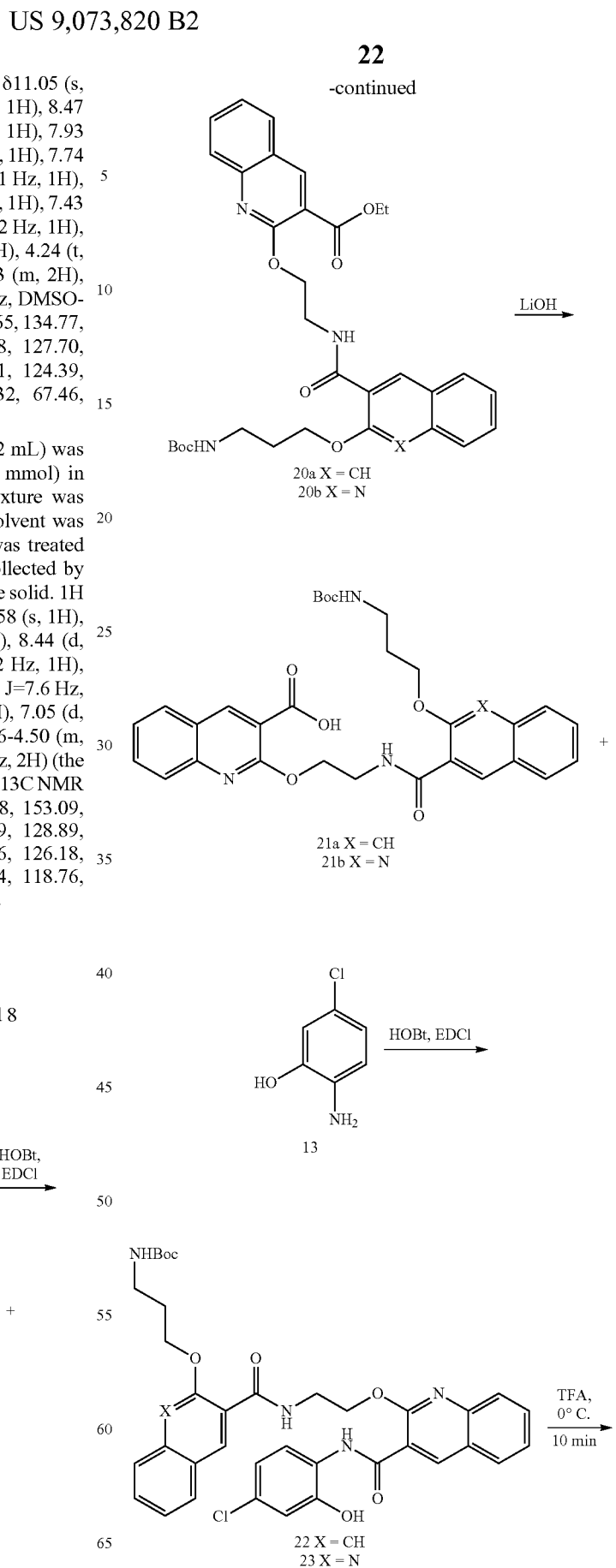

-continued

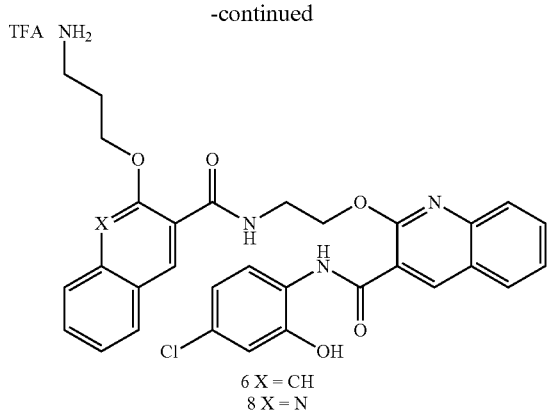

6 X = CH
8 X = N

Compound 19a: EDCl (265 mg, 1.2 mmol) and HOBt (181 mg, 1.2 mmol) were added to a stirred suspension of 12b (345 mg, 1.0 mmol) and 2-aminoethanol 18 (91.5 mg, 1.5 mmol) in dichloromethane (6 mL) at room temperature. The reaction mixture was stirred for overnight at room temperature. The reaction mixture was then diluted with water (30 mL) and extracted with ethyl acetate (60 mL). The organic layer was washed with brine (20 mL) and dried over $Na_2SO_4$. The solution was filtered and the solvent was removed to give a residue that was purified by flash column chromatography, eluting with hexanes-ethyl acetate (1:3) to give product 19a (350 mg, 90%) as a colorless oil: $^1$H NMR (400 MHz, CDCl$_3$) δ 8.73 (s, 1H), 8.57 (brs, 1H), 7.88 (d, J=8.1 Hz, 1H), 7.70 (d, J=8.2 Hz, 1H), 7.50 (t, J=7.6 Hz, 1H), 7.38 (t, J=7.6 Hz, 1H), 7.17 (s, 1H), 4.96 (t, J=5.1 Hz, 1H), 4.25 (t, J=6.4 Hz, 2H), 3.88 (q, J=4.9 Hz, 2H), 3.80-3.71 (m, 3H), 3.41 (q, J=6.9 Hz, 2H), 2.11 (quintet, J=6.4 Hz, 2H), 1.40 (s, 9H).

Compound 19b. EDCl (636 mg, 2.88 mmol) and HOBt (434 mg, 2.88 mmol) were added to a stirred suspension of 12c (836 mg, 2.42 mmol) and 2-aminoethanol (221 mg, 3.6 mmol) in dichloromethane (10 mL) at room temperature. The reaction mixture was stirred for overnight at room temperature. The reaction mixture was then diluted with water (30 mL) and extracted with ethyl acetate (100 mL). The organic layer was washed with brine (20 mL) and dried over $Na_2SO_4$. The solution was filtered and the solvent was removed to give a residue that was purified by flash column chromatography, eluting with dichloromethane-methanol (20:1) to give the product 19b (0.9 g, 95%) as a colorless oil: $^1$H NMR (400 MHz, CDCl$_3$) δ 9.00 (s, 1H), 8.72 (brs, 1H), 7.87 (d, J=8.0 Hz, 1H), 7.82 (d, J=8.3 Hz, 1H), 7.69 (t, J=7.5 Hz, 1H), 7.43 (t, J=7.5 Hz, 1H), 4.94 (t, J=5.2 Hz, 1H), 4.70 (t, J=5.4 Hz, 2H), 3.91-3.87 (m, 3H), 3.78-3.72 (m, 2H), 3.40 (q, J=6.9 Hz, 2H), 2.07 (quintet, J=5.9 Hz, 2H), 1.42 (s, 9H).

Compound 20a. To a solution of ethyl 2-hydroxyquinoline-3-carboxylate 9c (260 mg, 1.2 mmol), 19a (350 mg, 0.9 mmol) and PPh$_3$ (314 mg, 1.2 mmol) in THF (5 mL) was added a solution of DEAD (0.19 mL, 1.2 mmol) in THF (1 mL) dropwise at 0° C. The mixture was stirred at room temperature for overnight. The solvent was removed under reduced pressure and the residue was purified by flash column chromatography, eluting with hexanes-ethyl acetate (1:1) to give the product 20a (412 mg, 78%) as a colorless oil (note: this compound contains 3 eq of reduced DEAD, which can't separated from the product): $^1$H NMR (400 MHz, CDCl$_3$) δ 8.68 (s, 1H), 8.63 (s, 1H), 8.42 (brs, 1H), 7.87 (d, J=8.1 Hz, 1H), 7.82-7.78 (m, 2H), 7.73-7.67 (m, 2H), 7.49 (t, J=7.3 Hz, 1H), 7.42 (t, J=7.6 Hz, 1H), 7.37 (t, J=7.5 Hz, 1H), 7.18 (s, 1H), 5.10 (brs, 1H), 4.79 (t, J=5.0 Hz, 2H), 4.37 (q, J=7.2 Hz, 2H), a triplet of 2H is buried in reduced DEAD peak, 4.06 (q, J=5.2 Hz, 2H), 3.25 (q, J=5.3 Hz, 2H), 2.00 (quintet, J=6.3 Hz, 2H), 1.37 (t, J=7.3 Hz, 3H), 1.35 (s, 9H).

Compound 20b. To a solution of ethyl 2-hydroxyquinoline-3-carboxylate 9c (627 mg, 2.89 mmol), 19b (900 mg, 2.31 mmol) and PPh$_3$ (758 mg, 2.89 mmol) in THF (5 mL) was added a solution of DEAD (0.45 mL, 2.89 mmol) in THF (1 mL) dropwise at 0° C. The mixture was stirred at room temperature for overnight. The solid was precipitated from the reaction mixture and was collected by filtration and washed with ethyl acetate to give the acid 20b (236 mg, 17%) as a white solid. $^1$H NMR (400 MHz, CDCl$_3$) δ 8.99 (s, 1H), 8.73 (brs, 1H), 8.46 (s, 1H), 7.89-7.83 (m, 3H), 7.73-7.65 (m, 3H), 7.44 (t, J=7.7 Hz, 1H), 7.27 (t, J=7.6 Hz, 1H), 5.49 (brs, 1H), 4.79 (t, J=6.1 Hz, 2H), 4.66 (t, J=7.0 Hz, 2H), 4.43 (q, J=7.1 Hz, 2H), 3.89 (q, J=6.4 Hz, 2H), 3.28 (q, J=6.2 Hz, 2H), 2.03 (quintet, J=5.8 Hz, 2H), 1.43 (s, 9H), 1.42 (t, J=7.2 Hz, 3H).

Compound 21a. To a solution of 20a (412 mg, 0.70 mmol) in MeOH-THF-water (1:1:1, 15 mL) was added LiOH·H$_2$O (150 mg, 3.5 mmol) at 0° C. The resulting mixture was stirred at room temperature for overnight. The organic solvents were removed under reduced pressure and the residue was acidified with 2 N HCl to pH ~2 at 0° C. The reaction mixture was extracted with ethyl acetate (40 mL). The organic layer was then washed with brine (15 mL) and dried over $Na_2SO_4$. The solution was filtered and the solvent was removed to give the acid 21a (195 mg, 50%) as a colorless oil: $^1$H NMR (400 MHz, DMSO-d$_6$) δ 13.14 (brs, 1H), 8.73 (s, 1H), 8.50 (t, J=4.9 Hz, 1H), 8.29 (s, 1H), 8.02 (d, J=8.2 Hz, 1H), 7.92 (d, J=7.9 Hz, 1H), 7.83 (d, J=7.6 Hz, 1H), 7.80-7.73 (m, 2H), 7.55-7.47 (m, 2H), 7.44 (s, 1H), 7.39 (t, J=7.4 Hz, 1H), 6.90 (t, J=5.2 Hz, 1H), 4.65 (t, J=5.9 Hz, 2H), 4.16 (t, J=6.0 Hz, 2H), 3.81 (q, J=5.7 Hz, 2H), 3.09 (q, J=6.1 Hz, 2H), 1.87 (quintet, J=6.3 Hz, 2H), 1.29 (s, 9H).

Compound 21b. To a solution of 20b (232 mg, 0.39 mmol) in MeOH-THF-water (1:1:1, 15 mL) was added LiOH.H$_2$O (83 mg, 2.0 mmol) at 0° C. The resulting mixture was stirred at room temperature for overnight. The organic solvents were removed under reduced pressure and the residue was acidified with 2 N HCl to pH ~2 at 0° C. The reaction mixture was extracted with ethyl acetate (100 mL). The organic layer was then washed with brine (15 mL) and dried over $Na_2SO_4$. The solution was filtered and the solvent was removed to give the acid 21b (220 mg, 98%) as a white solid. $^1$H NMR (400 MHz, DMSO-d$_6$) δ 14.66 (brs, 1H), 8.90 (s, 1H), 8.74 (t, J=5.3 Hz, 1H), 8.55 (s, 1H), 8.06 (d, J=7.3 Hz, 1H), 7.80 (d, J=7.3 Hz, 1H), 7.97 (d, J=8.5 Hz, 1H), 7.82-7.70 (m, 3H), 7.48 (t, J=7.3 Hz, 1H), 7.40 (t, J=7.5 Hz, 1H), 6.96 (t, J=4.9 Hz, 1H), 4.64 (t, J=5.6 Hz, 2H), 4.47 (t, J=5.7 Hz, 2H), 3.75 (q, J=5.2 Hz, 2H), 3.03 (q, J=6.0 Hz, 2H), 1.83 (quintet, J=6.0 Hz, 2H), 1.31 (s, 9H).\

Compound 22. EDCl (97 mg, 0.44 mmol) and HOBt (67 mg, 0.44 mmol) were added to a stirred solution of 21a (190 mg, 0.34 mmol) and 2-amino-5-chlorophenol 13 (72 mg, 0.51 mmol) in dichloromethane (5 mL) at room temperature. The reaction mixture was stirred for overnight at room temperature. The reaction mixture was then diluted with water (30 mL) and was extracted with ethyl acetate (60 mL). The organic layer was washed with brine (20 mL) and dried over $Na_2SO_4$. The solution was filtered and the solvent was removed to give a residue that was purified by flash column chromatography, eluting with dichloromethane-ethyl acetate (5:1) to give the product 22 (151 mg, 65%) as a white solid. $^1$H NMR (400 MHz, DMSO-d$_6$) δ 10.97 (s, 1H), 10.60 (s, 1H), 9.10 (s, 1H), 8.61 (d, J=5.4 Hz, 1H), 8.44 (d, J=8.3 Hz, 1H), 8.19 (s, 1H), 8.14 (d, J=7.9 Hz, 1H), 7.86-7.76 (m, 4H), 7.54 (t, J=7.2 Hz, 1H), 7.50 (t, J=7.9 Hz, 1H), 7.37 (s, 1H), 7.36 (t, J=7.8 Hz, 1H), 6.92-6.88 (m, 2H), 6.83 (t, J=5.5 Hz, 1H), 4.83 (t, J=5.7 Hz, 2H), 4.07 (t, J=5.8 Hz, 2H), 4.01 (q, J=5.7 Hz, 2H), 3.01 (q, J=5.5 Hz, 2H), 1.79 (quintet, J=6.3 Hz, 2H), 1.23 (s, 9H); $^{13}$C NMR (100 MHz, DMSO-$d_6$) δ 165.64, 160.51, 157.22, 155.64, 153.44, 147.73, 146.52, 143.24, 134.91, 132.08, 130.70, 129.22, 128.26, 127.68, 127.34, 127.28, 126.40, 126.31, 125.93, 125.23, 125.20, 124.60, 124.18, 120.81, 118.85, 117.34, 114.27, 107.17, 77.48, 65.65, 39.26, 38.28, 36.49, 28.70, 28.03?.

Compound 23. EDCl (112 mg, 0.51 mmol) and HOBt (78 mg, 0.51 mmol) were added to a stirred suspension of 21b (220 mg, 0.39 mmol) and 2-amino-5-chlorophenol 13 (84 mg, 0.59 mmol) in dichloromethane (5 mL) at room temperature. The reaction mixture was stirred for overnight at room temperature. The reaction mixture was then diluted with water (30 mL) and was extracted with ethyl acetate (60 mL). The organic layer was washed with brine (20 mL) and dried over $Na_2SO_4$. The solution was filtered and the solvent was removed to give a residue that was purified by flash column chromatography, eluting with dichloromethane-ethyl acetate (5:1) to give the product 23 (70 mg, 26%) as a yellow solid. $^1$H NMR (400 MHz, CDCl$_3$) δ 12.60 (s, 1H), 10.19 (s, 1H), 9.02 (s, 2H), 8.88 (t, J=5.0 Hz, 1H), 8.03 (d, J=8.7 Hz, 1H), 7.87 (d, J=7.8 Hz, 1H), 7.82 (d, J=8.6 Hz, 1H), 7.80 (d, J=8.6 Hz, 1H), 7.74 (t, J=7.2 Hz, 1H), 7.71 (t, J=7.7 Hz, 1H), 7.45 (t, J=7.5 Hz, 1H), 7.34 (t, J=7.4 Hz, 1H), 6.92-6.887.18 (d, J=8.0 Hz, 1H), 7.05 (d, J=1.5 Hz, 1H), 6.84 (dd, J=8.7, 1.9 Hz, 1H), 4.94 (t, J=5.8 Hz, 1H), 4.78 (t, J=6.6 Hz, 2H), 4.73 (t, J=5.8 Hz, 2H), 3.96 (q, J=5.9 Hz, 2H), 3.21 (q, J=6.1 Hz, 2H), 1.98 (quintet, J=5.7 Hz, 2H), 1.42 (s, 9H); $^{13}$C NMR (100 MHz, CDCl$_3$) δ 164.56, 162.05, 161.76, 157.26, 156.07, 149.46, 146.72, 144.81, 142.95, 140.21, 133.61, 131.39, 131.19, 130.68, 128.41, 126.29, 124.55, 124.34, 123.19, 122.99, 119.65, 119.35, 119.05, 118.90, 116.36, 114.90, 79.18, 62.48, 41.48, 37.76, 36.22, 29.36, 27.92.

Compound 6. TFA (1 mL) was added to the flask containing 22 (30 mg, 0.044 mmol) at 0° C. The resulting mixture was stirred for 10 min at 0° C. The reaction was quenched with water (10 mL) and the solid was collected by filtration to give product 6 (28 mg, 93%) as a white solid. $^1$H NMR (400 MHz, DMSO-$d_6$) δ 11.08 (s, 1H), 10.63 (s, 1H), 9.10 (s, 1H), 8.77 (t, J=5.6 Hz, 1H), 8.45 (d, J=8.6 Hz, 1H), 8.17 (d, J=7.9 Hz, 1H), 7.91 (s, 1H), 7.86 (d, J=7.6 Hz, 1H), 7.83 (d, J=7.8 Hz, 1H), 7.80 (d, J=8.2 Hz, 1H), 7.76 (brs, 3H), 7.58-7.48 (m, 3H), 7.39 (s, 1H), 7.33 (t, J=7.6 Hz, 1H), 6.96 (d, J=2.1 Hz, 1H), 6.93 (dd, J=8.8, 2.2 Hz, 1H), 4.86 (t, J=5.8 Hz, 2H), 4.21 (t, J=5.8 Hz, 2H), 3.92 (q, J=5.8 Hz, 2H), 2.99 (q, J=5.5 Hz, 2H), 2.03 (quintet, J=6.1 Hz, 2H); $^{13}$C NMR (100 MHz, DMSO-$d_6$) δ 166.78, 160.73, 157.24, 153.01, 147.83, 146.45, 143.14, 134.62, 132.14, 129.60, 129.27, 127.94, 127.68, 127.40, 127.27, 126.38, 126.15, 125.96, 125.29, 124.62, 124.31, 120.94, 118.93, 117.69, 114.42, 107.19, 66.02, 65.33, 38.30, 37.03, 26.18.

Compound 8. TFA (1 mL) was added to the flask containing 23 (28 mg, 0.041 mmol) at 0° C. The resulting mixture was stirred for 10 min at 0° C. The reaction was quenched with water (10 mL) and the solid was collected by filtration to give product 8 (22 mg, 79%) as a yellow solid. $^1$H NMR (400 MHz, DMSO-$d_6$) δ 12.34 (s, 1H), 10.78 (s, 1H), 9.04 (s, 1H), 8.84 (t, J=5.0 Hz, 1H), 8.49 (d, J=8.3 Hz, 1H), 8.37 (s, 1H), 8.11 (d, J=8.2 Hz, 1H), 7.98 (d, J=8.9 Hz, 1H), 7.88-7.69 (m, 7H), 7.46-7.38 (m, 2H), 6.97 (s, 1H), 6.91 (d, J=8.6 Hz, 1H), 4.65 (t, J=4.8 Hz, 2H), 4.55 (t, J=4.8 Hz, 2H), 3.70 (q, J=4.2 Hz, 2H), 3.01 (q, J=6.1 Hz, 2H), 2.08 (quintet, J=5.8 Hz, 2H); $^{13}$C NMR (100 MHz, DMSO-$d_6$) δ 165.32, 161.55, 160.67, 157.58, 147.82, 145.92, 144.34, 140.20, 139.67, 133.48, 131.29, 131.25, 128.38, 127.08, 126.37, 126.14, 124.86, 123.93, 123.15, 120.93, 120.68, 120.15, 119.57, 118.82, 115.09, 114.35, 68.87, 41.62, 36.95, 26.25.

What is claimed is:

1. A compound with the structure:

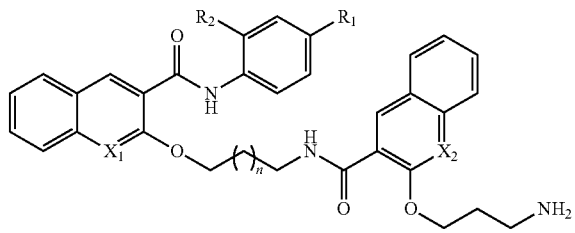

wherein n is an integer selected from 0 and 1, wherein $R_1$ is halo, wherein $R_2$ is OH or halo, and wherein $X_1$ and $X_2$ are independently CH or N.

2. The compound of claim 1 wherein $R_1$ is Cl.
3. The compound of claim 2 wherein n =1.
4. The compound of claim 3 wherein $X_1$ is CH, wherein $X_2$ is CH, and wherein $R_2$ is OH.
5. The compound of claim 2 wherein n =0.
6. The compound of claim 5 wherein $R_2$ is OH.
7. The compound of claim 6 wherein $X_1$ is CH and wherein $X_2$ is CH.
8. The compound of claim 6 wherein $X_1$ is N and wherein $X_2$ is CH.
9. The compound of claim 6 wherein $X_1$ is CH and wherein $X_2$ is N.
10. The compound of claim 5 wherein $X_1$ is N and wherein $X_2$ is N.
11. The compound of claim 5 wherein $X_1$ is N, wherein $X_2$ is N and wherein $R_2$ is F.
12. A pharmaceutical composition comprising an effective amount of the compound of claims 1 or a pharmaceutically acceptable salt thereof and a pharmaceutically acceptable carrier.
13. A method of treating cancer comprising: administering an effective amount of the pharmaceutical composition of claim 12 to a subject with cancer, thereby treating the cancer.
14. The method of claim 13 further comprising administering the pharmaceutical composition intravenously.
15. The method of claim 14 wherein the effective amount is greater than 2 mg/kg.
16. The method of claim 13 further comprising administering the pharmaceutical composition orally.
17. The method of claim 16 wherein the effective amount is greater than 20 mg/kg.
18. The method of claim 13 wherein the subject has lung cancer, prostate cancer or breast cancer.
19. The method of claim 13 wherein the subject is human.
20. The method of claim 13 wherein the pharmaceutical composition comprises the compound of claim 4.

* * * * *